(12) United States Patent
Watanabe et al.

(10) Patent No.: US 9,322,741 B2
(45) Date of Patent: Apr. 26, 2016

(54) EXHAUST GAS ANALYZING SYSTEM

(71) Applicant: HORIBA, Ltd., Kyoto (JP)

(72) Inventors: Koji Watanabe, Kyoto (JP); Tetsu Yoshioka, Kyoto (JP)

(73) Assignee: HORIBA, Ltd., Kyoto (JP)

( * ) Notice: Subject to any disclaimer, the term of this patent is extended or adjusted under 35 U.S.C. 154(b) by 3 days.

(21) Appl. No.: 13/901,214

(22) Filed: May 23, 2013

(65) Prior Publication Data
US 2013/0312489 A1 Nov. 28, 2013

(30) Foreign Application Priority Data

May 23, 2012 (JP) .................................. 2012-118094

(51) Int. Cl.
*G01M 15/10* (2006.01)
*G01N 1/22* (2006.01)
*G01N 33/00* (2006.01)

(52) U.S. Cl.
CPC ........... *G01M 15/102* (2013.01); *G01N 1/2252* (2013.01); *G01N 33/0004* (2013.01)

(58) Field of Classification Search
CPC ............................ G01M 15/10; G01M 15/102
USPC ......................................................... 73/23.31
See application file for complete search history.

(56) References Cited

U.S. PATENT DOCUMENTS

| 7,530,013 B2* | 5/2009 | Bushel et al. ................. 715/212 |
| 2002/0005903 A1* | 1/2002 | Miyamoto et al. ............ 348/232 |

FOREIGN PATENT DOCUMENTS

| JP | 08-101204 | 4/1996 |
| JP | 2002-082119 | 3/2002 |
| JP | 2003-194702 | 7/2003 |
| JP | 2004-028932 | 1/2004 |
| JP | 2007-101351 | 4/2007 |
| JP | 2010276473 | 12/2010 |
| JP | 2011-075468 | 4/2011 |

* cited by examiner

*Primary Examiner* — Laura Martin
*Assistant Examiner* — Alex Devito
(74) *Attorney, Agent, or Firm* — Brooks Kushman P.C.

(57) ABSTRACT

The present invention provides an exhaust gas analyzing system having a function of navigating an adjusting procedure of a gas analyzer, and the system includes an analyzer for analyzing exhaust gas and a manager for managing or controlling the analyzer, and the manager includes a procedure display part for selectively displaying adjustment items necessary for adjustment of the analyzer in a predetermined order in a predetermined area of one screen, and a detail input screen display part for displaying a detail input screen of the selected adjustment item.

4 Claims, 5 Drawing Sheets

EXHAUST GAS ANALYZING SYSTEM

CROSS-REFERENCE TO RELATED APPLICATION

This application claims priority to JP Application No. 2012-118094, filed on May 23, 2012, the disclosure of which is incorporated in its entirety by reference herein.

TECHNICAL FIELD

The present invention relates to an exhaust gas analyzing system for analyzing exhaust gas discharged from internal combustion engines of automobiles and the like.

BACKGROUND ART

In a conventional exhaust gas analyzing system for analyzing the exhaust gas discharged from internal combustion engines of automobiles and the like, an automobile mounted on chassis dynamo apparatus is travelled in a predetermined travelling mode by means of an automatic operating robot, discharged exhaust gas is collected by a constant-volume sampling device, and collected sample gas is supplied to an exhaust gas measuring device equipped with a plurality of different gas analyzers having different measurement principles, and measured for each component.

For this type of exhaust gas analyzing system, in order to obtain an accurate measurement result, periodical adjustment of the gas analyzers is required. In the adjustment of each gas analyzer, various adjustments such as light quantity balance adjustment, gain adjustment, and offset adjustment need to be performed in a correct order. When the order is not satisfied, the same adjusting operations must be performed again. However, the adjusting operations are cumbersome and complicated for less-experienced operators and thus, it is difficult to make various adjustments in the correct order. In addition, the gas analyzers of different types require different adjusting procedures, and proper setting of the procedures takes a lot of time and efforts even for experienced operators.

SUMMARY

Technical Problem

Thus, an object of the present invention is to provide an exhaust gas analyzing system having a function of navigating an adjusting procedure of a gas analyzer. Another object of the present invention is to provide an exhaust gas analyzing system capable of decreasing time and efforts for adjustment of the gas analyzer to the minimum necessary.

Solution to Problem

An exhaust gas analyzing system according to the present invention includes an analyzer for analyzing exhaust gas and a manager for managing or controlling the analyzer, wherein the manager includes a procedure display part for selectively displaying adjustment items necessary for adjustment of the analyzer in a predetermined order in a predetermined area of one screen, and a detail input screen display part for displaying a detail input screen of the selected adjustment item.

For such system, the operator can made adjustment while being navigated by an adjusting procedure displayed on the procedure display part. For this reason, even less-experienced operators can properly perform the adjusting operation, which is very convenient.

Further, since various adjustment conditions for each adjustment item can be freely set on the detail input screen display part, highly-accurate adjustment can be made according to circumstances.

Further, even when the plurality of different analyzers having different measurement principles are provided as the above-mentioned analyzer, according to the present invention, the plurality of analyzers can be adjusted in a correct order. Furthermore, in the case where interference correction of the measurement target component with other components is needed, when the plurality of analyzers are provided, adjustment related to the interference correction may have dependency. In such case, the effect of the present invention is large.

The adjustment items have different adjustment frequencies. Some adjustment items have a high degree of independence, other adjustment items have a high degree of dependence. For this reason, it is preferred that the order of the plurality of adjustment item is determined based on the adjustment frequencies and the dependence between the adjustment items. For example, the items having a high adjustment frequency may be arranged first in the order, and the items that are highly dependent on each other may be consecutively arranged. By arranging the adjustment items in this manner, time and efforts for adjustment can be decreased to the minimum necessary.

Advantageous Effects of Invention

As described above, according to the present invention, since the adjusting operation can be performed in the correct order irrespective of the operator's skill, the exhaust gas can be efficiently analyzed.

DESCRIPTION OF EMBODIMENTS

An embodiment of the present invention will be described below with reference to figures.

Figure 1:
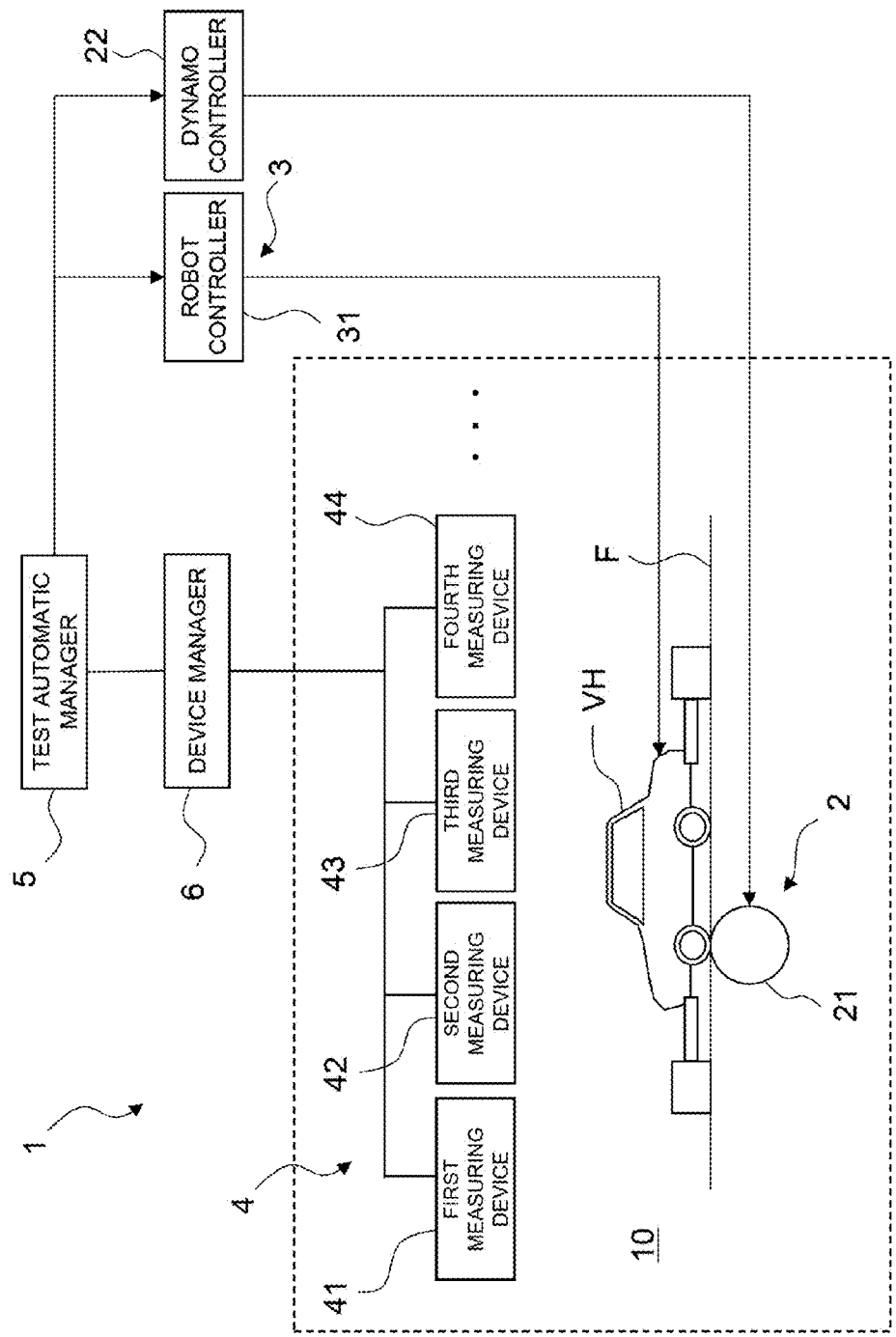
FIG. 1 is a schematic overall view of an exhaust gas analyzing system in accordance with an embodiment of the present invention.

FIG. 1 schematically shows an entire exhaust gas analyzing system 1 in accordance with this embodiment. The exhaust gas analyzing system 1, as shown in this figure, includes a chassis dynamometer 2, an automatic driving device 3, a test automatic manager 5, a plurality of exhaust gas measuring devices 4, and a device manager 6. A vehicle VH can be travelled on the chassis dynamometer 2 in a pseudo manner, and performances of the vehicle VH, such as fuel consumption and exhaust gas components, can be tested.

Each of the parts will be described below. The chassis dynamometer 2 includes a uniaxial rotating drum 21, a motor and a flywheel (not shown) that apply loads on the rotating drum 21, and a dynamo controller 22 for controlling them.

The rotating drum 21 and the motor or the flywheel are placed in a pit below a floor F of a test chamber 10, and a top of the rotating drum 21 is exposed from an opening formed on the floor F of the test chamber 10. Driving wheels of the vehicle VH are located at test positions immediately above the top of the rotating drum 21 such that the vehicle VH can travel as if it actually travels. The dynamo controller 22 is accommodated in a measurement chamber provided, for example, adjacent to the test chamber 10. The test chamber 10 and the measurement chamber (and the pit) are collectively referred to as a cell.

The automatic driving device 3 includes a driving robot (not shown) that is mounted in a cabin of the vehicle VH and drives an accelerator, a brake, and a clutch, and a robot controller 31 that is connected to the driving robot and controls the driving robot, and the automatic driving device 3 sends various command signals to the robot controller 31, thereby controlling the driving robot to cause the vehicle VH to automatically travel in one or more travelling modes such as a 10 mode and a LA mode. The robot controller 31 is accommodated in, for example, the measurement chamber.

Though not described in detail, the test automatic manager 5 basically serves to set a schedule of a travelling test. Examples of setting the schedule of the travelling test include setting of a test mode and a test date, more detailed setting of vehicle behaviors such as vehicle speed and engine rotating speed, and setting of a measurement target and measurement timing. The test automatic manager is provided with a communication port, and the measuring devices 4, the chassis dynamometer 2, and the automatic driving device 3 are connected to the test automatic manager 5 so as to be intercommunicable in a wired or wireless manner.

When the operator sets the schedule in this manner, the test automatic manager 5 appropriately transmits the command signal to the chassis dynamometer 2, the automatic driving device 3, and the device manager 6 according to the schedule, and controls them such that the test is made as scheduled.

Although one device manager 6 is connected to the test automatic manager 5 in FIG. 1, a plurality of device managers 6 may be connected to the test automatic manager 5. In this case, the test automatic manager 5 can perform scheduling for each of the device managers 6.

The exhaust gas measuring devices 4 (hereinafter also referred to merely measuring devices 4) are devices used to measure the exhaust gas, and include, for example, a device configured of one or more gas analyzers as unit equipment to measure exhaust gas components, and a device such as a constant-volume sampling device that makes pretreatment of measuring exhaust gas components.

In this embodiment, plural types of measuring devices 4 are adopted. For example, a first measuring device 41 including a plurality of different gas analyzers having different measurement principles, a second measuring device 42 as a constant-volume sampling device, a third measuring device 43 as an EGR rate measuring device, and a fourth measuring device 44 as an ultrasonic flow rate meter are provided. Examples of the gas analyzer include an FID for measuring THC, a CLD for measuring $NO_x$, and an NDIR for measuring CO and $CO_2$.

Each of the measuring devices 4 includes a sampling pipe for sampling intake gas or exhaust gas from an intake/exhaust path of an automobile internal combustion engine, measures the amount of each of components such as HC, $NO_x$, CO and $CO_2$ in gas sampled through the sampling pipe, and calculate performance values (ex. fuel consumption, EGR rate) of elements constituting the automobile, such as the internal combustion engine and a catalyst, on the basis of measurement values.

Thus, each of the measuring devices 4 includes a measuring sensor and a local computer, and the local computer functions as a calculating part for applying correction or calibration of an output value from the sensor to calculate the measurement value indicating the amount of each component, and calculating the equipment performance value on the basis of the measurement value, and as a communicating part for transmitting the measurement value and the equipment performance value, which are calculated by the calculating part, to the device manager 6 according to a predetermined protocol.

The local computer further includes a mode control part 402 for receiving the command signal from the device manager 6 and controlling an operation mode (measurement mode, calibration mode, purge mode, etc.) and a status mode (sleep mode, standby mode, etc.) of the exhaust gas measuring devices 4, a calibrating part for calibrating the sensor, or a local storing part for storing device status information of the measuring devices 4 up to now, such as pump pressure information indicating a suction pressure of a built-in pump, sensitivity information related to the sensitivity of the sensor, accumulated operating time information indicating accumulated operating time of each part, and inspection date identifying information for identifying a predetermined inspection time and date of the measuring devices 4.

Figure 2:
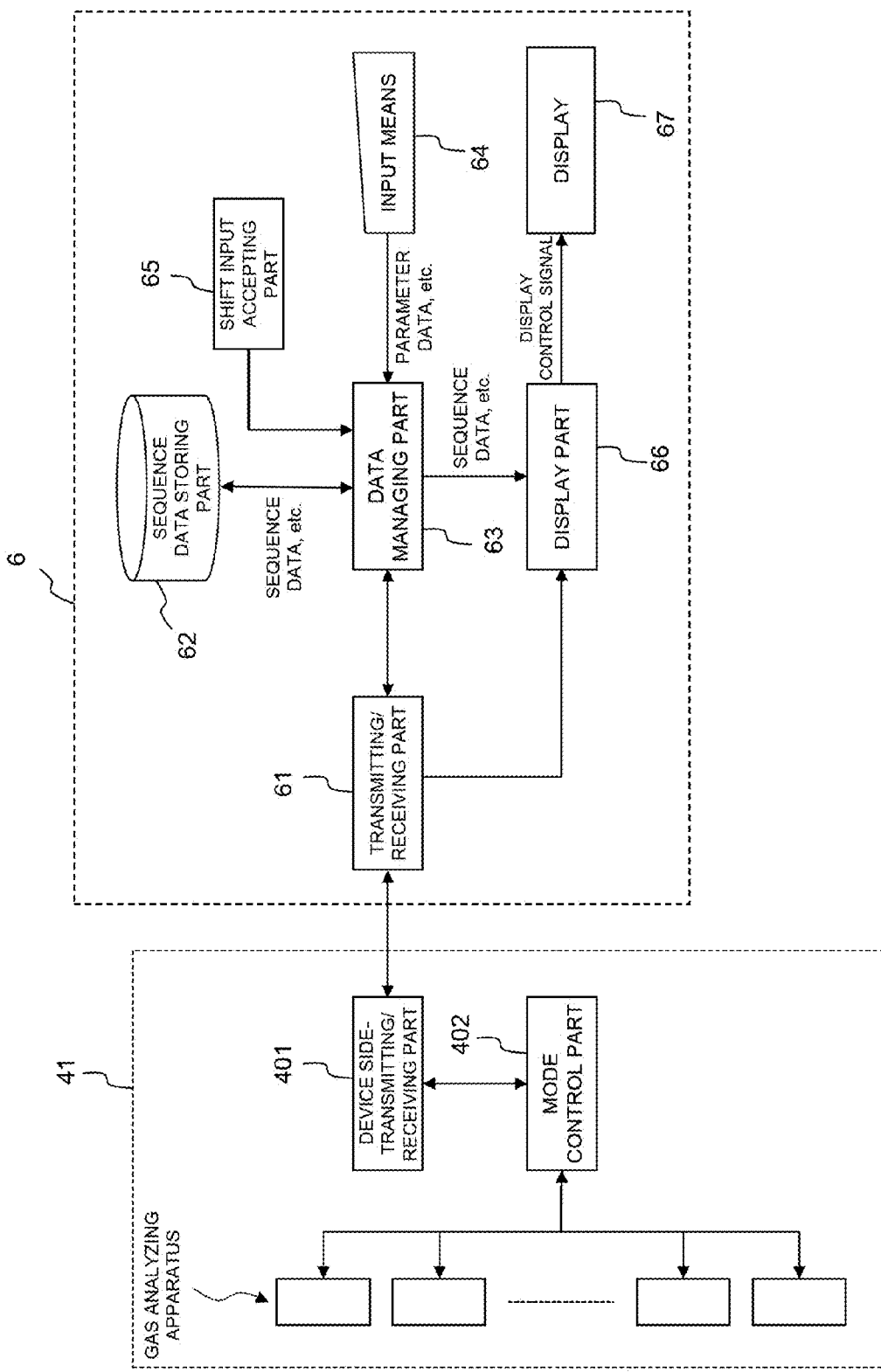
FIG. 2 is a functional block diagram of a device manager and exhaust gas measuring devices in the embodiment.

The device manager 6 is formed by, for example, installing a predetermined program into a general-purpose computer, and physically includes a CPU, a memory, a display 67, input means (keyboard, mouse and the like) 64, and a communication interface. Then, the CPU and peripheral devices cooperate according to the program stored in the memory such that the device manager 6 functions as a connection/disconnection monitoring part, a device indicator display part, and a device information acquiring part, and further, in this embodiment, as shown in FIG. 2, as a transmitting/receiving part 61, a data managing part 63, a shift input accepting part 65, a display part 66, and a sequence data storing part 62. The device manager 6 is provided with a communication port, and the measuring devices 4 are connected to the device manager 6 so as to be intercommunicable in a wired or wireless manner.

Each part of the device manager 6 will be described below in detail.

Figure 3:
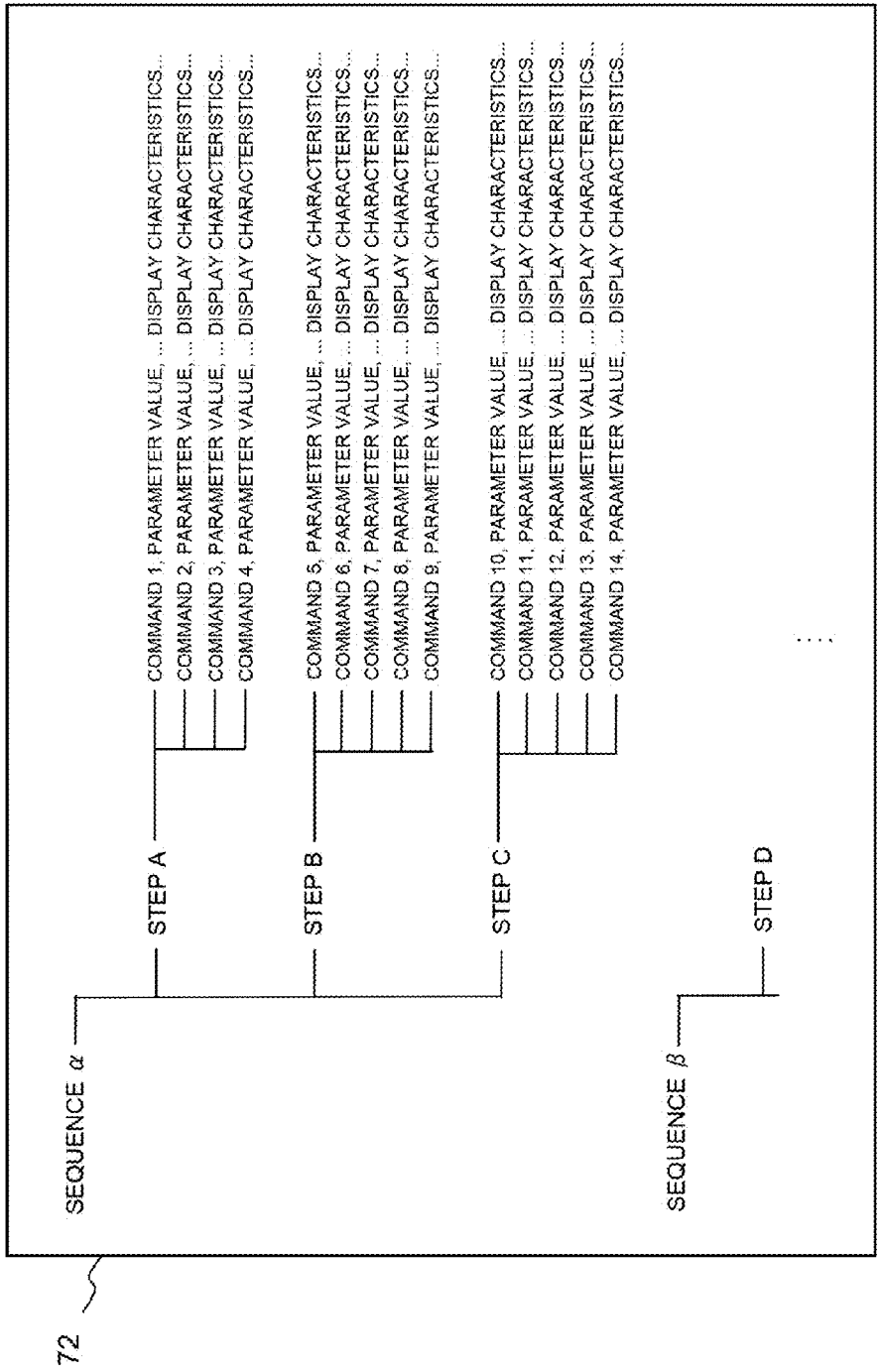
FIG. 3 is a view of a data structure of a sequence data storing part in the embodiment.

The sequence data storing part 62 is set in a predetermined area of the memory, and stores one or more pieces of sequence data indicating an adjustment procedure for each of the gas analyzers included in the exhaust gas measuring device 41. In the sequence data, an example of which is shown in FIG. 3, a plurality of step names are described in an execution order, and commands constituting the steps and parameter values necessary for the commands are described in a lower layer than the layer of each step name. The different steps have different adjustment frequencies. Some steps have a high degree of independence, and other steps have a high degree of dependence. For this reason, the order of the plurality of step names is not merely the execution order, but is defined based on the adjustment frequencies and the dependence of one adjustment item on another adjustment item so as to decrease time and efforts for adjustment to the minimum necessary. For this reason, for example, the steps having a high adjustment frequency are arranged first in the order, and the steps that are highly dependent on each other are consecutively arranged.

The step refers to each adjustment item to be performed for each gas analyzer, and the command refers to one or more instruction codes for instructing an adjustment element (for example, setting of a light source, setting of a gain value) constituting each adjustment item (step). In each step, the execution order of the commands is not necessarily defined.

The data managing part 63 serves to manage various types of data. For example, the data managing part 63 acquires sequence data selected or predetermined by the operator from the sequence data storing part 62, acquires parameter values set on a below-mentioned detail input screen G2 and adds the values to the command, and newly stores or updates the sequence data set on the detail input screen G2 in the sequence data storing part 62.

The display part 66 controls the display 67, and includes a procedure display function (function as a procedure display part) and a detail input screen display function (function as a detail input screen display part). The procedure display function is a function of displaying a procedure display screen G1 showing a plurality of step names described in sequence data acquired by the data managing part 63 in the execution order. The detail input screen display function is a function of displaying the detail input screen G2 for inputting parameters required to set contents of each step described in the sequence data acquired by the data managing part 63.

The transmitting/receiving part 61 is configured using the communication interface, transmits one or more commands constituting each step along with the corresponding parameters to the exhaust gas measuring device 41 (each gas analyzer), and receives a result of adjustment (step) made by each gas analyzer on the basis of the transmitted command.

The shift input accepting part 65 accepts a shift instruction input to another step from the operator or automatically, and when the shift instruction input is accepted, the display part 66 displays the detail input screen G2 corresponding to the indicated another step.

Next, a method of adjusting the exhaust gas analyzing system 1 having the above-mentioned configuration will be described below.

First, the operator performs a necessary initial operation, such as selection of sequence data, on an initial screen (detail are omitted) displayed on the display 67 of the device manager 6 by use of the input means 64. Then, the data managing part 63 acquires the sequence data selected by the operator from the sequence data storing part 62.

Figure 4:
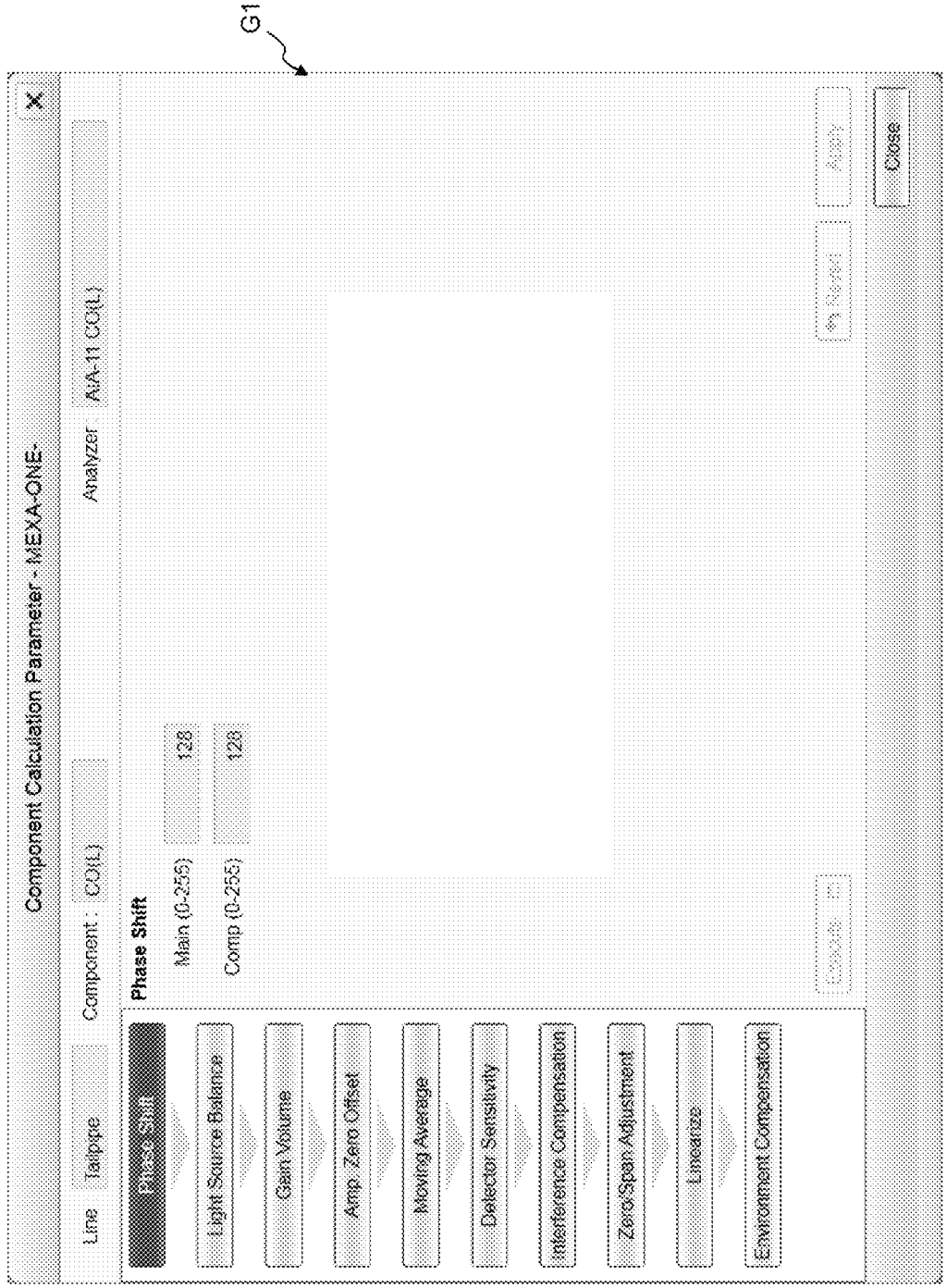
FIG. 4 is an explanation drawing for illustrating a procedure display screen for adjustment items in the embodiment.

Next, the display part 66 displays a window of the procedure display screen G1 as shown in FIG. 4. In displaying the screen, the display part 66 interprets the selected sequence data, and displays names of all steps described in the sequence data in a flow chart according to the adjusting procedure. When a certain step is selected on the procedure display screen G1, the selected step is highlighted, and as shown in FIG. 5, a window of the detail input screen G2 is also displayed, and detailed contents and parameters to be inputted of the highlighted step is displayed on the detail input screen G2.

Figure 5:
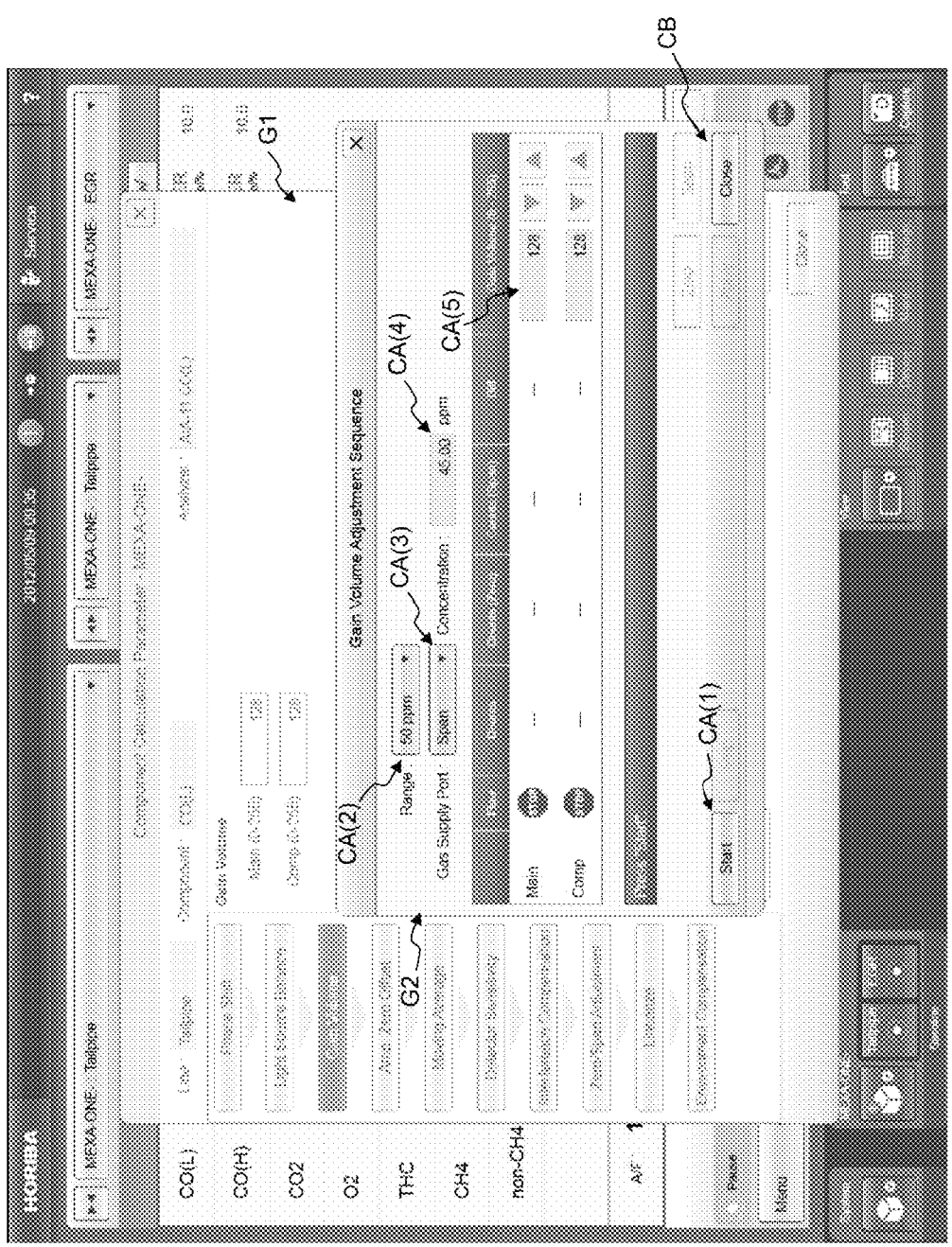
FIG. 5 is an explanation drawing for illustrating a detail input screen at execution of a gain value adjusting step in the embodiment.

On the detail input screen G2 shown in FIG. 5, a sign CA (2) represents an input column for a parameter designating a calibration concentration range, CA (3) represents an input column for a parameter designating the type of calibration gas, CA (4) represents an input column for a parameter designating the concentration of the calibration gas, and CA (5) represents an input column for a parameter designating a gain value as an output value per gas concentration. In this embodiment, the input columns of CA (2) and CA (3) each are formed of a list from which the operator can selectively input a predetermined value, and an input column of CA (5) is formed of a spin button that enables addition and subtraction with a click.

Next, when the operator inputs the parameter value in each of the input columns CA (2), CA (3), CA (4), and CA (5), and presses an execution button CA (1) set on the detail input screen G2, the data managing part 63 acquires the inputted parameter values, and adds the values to one or more commands necessary for execution of the step.

Then, the transmitting/receiving part 61 transmits the commands with the parameters to the exhaust gas measuring device 41. When the execution of the step is stopped, a completion button CB may be pressed.

In the exhaust gas measuring device 41, a device side-transmitting/receiving part 401 receives the transmitted commands and the like, and the mode control part 402 interprets the commands and the like to adjust and monitor/control an open/close valve of a calibration gas supply source and a suction pump of each gas analyzer, and so on.

Upon shifting to another step, the operator may select (click) another step on the procedure display screen G1. When the shift input accepting part 65 accepts a signal generated by this operation input, the current step shifts to another step, and the detail input screen G2 corresponding to the new step is displayed. The steps may be executed according to the order displayed on the procedure display screen G1, but any unnecessary step may be omitted. When the order of the selected step is wrong, a warning light or warning sound may be made to stop operation.

For the exhaust gas analyzing system 1 thus configured in this embodiment, the operator can make adjustment while being navigated by the adjusting procedure displayed on the procedure display screen G1. For this reason, even by less-experienced operators, or even when the plural types of different gas analyzers having different measurement principles are provided, the adjusting operation can be properly performed, which is very convenient. Especially in the case where interference correction between the measurement target component and other components is needed, when the plural types of analyzers are provided, adjustment related to the interference correction may have dependency. However, even in this case, according to the present invention, the adjusting operation can be properly performed and effect of the present invention is more remarkable.

Further, since various adjustment conditions can be freely set on the detail input screen G2 in each of the adjusting steps, highly-accurate adjustment can be made according to circumstances.

The present invention is not limited to the above-mentioned embodiment.

According to the present invention, a plurality of exhaust gas measuring devices may be connected to the device manager, and one device manager may manage or control the plurality of exhaust gas measuring devices.

Addition, deletion, and change in the order with respect to the steps described in the sequence data may be made. In this case, a change history may be stored, and reused in subsequent adjusting operations.

Although the sequence data is stored in the device manager in the embodiment, the sequence data may be stored in the exhaust gas measuring device, and when the exhaust gas measuring device is connected to the device manager, the device manager may read the sequence data.

Further, each input column of the parameter may be a slide bar that can designate a value according to the position of the bar in a number line, and one window may be divided into two screens such that the procedure display screen and the detail input screen can be displayed together in one window.

The present invention can be variously modified without deviating from its subject matter.

REFERENCE SIGNS LIST

1: exhaust gas analyzing system
41: first measuring device (exhaust gas measuring device)
6: device manager
G1: procedure display screen
G2: detail input screen While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. An exhaust gas analyzing system comprising:
   an analyzer for analyzing exhaust gas; and
   a manager for managing or controlling the analyzer, wherein the manager includes a procedure display part for selectively displaying, in a predetermined area of one screen, adjustment items necessary for adjustment of the analyzer in an order that is determined according to an interdependence of the adjustment items such that the adjustment items that affect a greater number of other of the adjustment items appear earlier in the order as compared with the adjustment items that affect a lesser number of other of the adjustment items, and a detail input screen display part for displaying a detail input screen of a selected adjustment item.

2. The exhaust gas analyzing system according to claim 1, wherein a plurality of different analyzers having different measurement principles are provided.

3. The exhaust gas analyzing system according to claim 1, wherein the order is further determined according to adjustment frequencies of the adjustment items.

4. An adjustment items display method used for an exhaust gas analyzing system that includes an analyzer for analyzing exhaust gas and a manager for managing or controlling the analyzer, the method comprising:
   selectively displaying, by the manager in a predetermined area of one screen, adjustment items necessary for adjustment of the analyzer in an order that is determined according to an interdependence of the adjustment items such that the adjustment items that affect a greater number of other of the adjustment items appear earlier in the order as compared with the adjustment items that affect a lesser number of other of the adjustment items; and
   displaying, by the manager, a detail input screen of a selected adjustment item.

\* \* \* \* \*